United States Patent [19]

Stephenson et al.

[11] Patent Number: 5,468,644
[45] Date of Patent: Nov. 21, 1995

[54] SPECTROSCOPIC INVESTIGATION USING ORGANOMETALLIC COMPOUNDS

[75] Inventors: George R. Stephenson, Norwich; Colin S. Creaser, Wymondham, both of England

[73] Assignee: British Technology Group Limited, London, England

[21] Appl. No.: 146,063

[22] PCT Filed: May 7, 1992

[86] PCT No.: PCT/GB92/00825

§ 371 Date: Nov. 9, 1993

§ 102(e) Date: Nov. 9, 1993

[87] PCT Pub. No.: WO92/19968

PCT Pub. Date: Nov. 12, 1992

[30] Foreign Application Priority Data

May 9, 1991 [GB] United Kingdom ............... 9110017

[51] Int. Cl.⁶ .................................................. G01N 31/22
[52] U.S. Cl. .............................. 436/163; 436/39; 436/41; 436/61; 436/100; 436/166
[58] Field of Search ................... 436/39, 41, 61, 436/100, 163, 166

[56] References Cited

U.S. PATENT DOCUMENTS 4,656,142 4/1987 Jaouen et al. ..................... 436/501

FOREIGN PATENT DOCUMENTS

| 0105785 | 4/1984 | European Pat. Off. . |
| 0345153 | 12/1989 | European Pat. Off. . |
| WO88/05439 | 1/1988 | WIPO . |
| WO88/07684 | 3/1988 | WIPO . |
| WO89/10372 | 4/1989 | WIPO . |

OTHER PUBLICATIONS

M. Salmain et al. "(N–succinimidyl 4–pentynoate) . . . " Bioconjugate Chem. vol. 2 No. 1, 1991, pp. 13–15.
G. Jaouen et al. "Metal carbonyl fragments . . . " Jour of the Am Chem Soc., vol. 107 No. 16 (16 Aug. 1985), pp. 4778–4780.
F. Le Borgne et al. "Cobalt–carbonyl complexes . . . " Tethedron Letters, vol. 29 No. 44 (1988), pp. 5649–5652.
K. Erdmann et al. "Adsorption of carbonyls on . . . " Chemical Abstracts #216628, vol. 109 No. 24 (12 Dec. 1988), p. 371.
D. M. Adams *Spectr., Rept. Conf. Hydrocarbon Res. Group Inst. Petrol.*, London, 1962, 265–278.
D. M. Adams *Chem. Abstr.* 1969, 70, 52537v.
S. Cenini et al. *Gazz. Chim. Ital.* 1972, 102, 141–163.
B. V. Lokshin et al. *J. Organomet. Chem.* 1972, 37, 331–337.
F. van Meurs et al. *J. Organomet. Chem.* 1976, 113, 353–359.
J. Korppi–Tommola et al. *Can. J. Chem.* 1979, 57, 2707–2712.
A. Meyer et al. *Organomettalics* 1984, 3, 1112–1118.
J. M. Bjerga et al., *Anal. Chem.* 1990, 62, 226–233.
T. A. Weil et al. *Inorg. Chem.* 1969, 8, 1002–1004.
S. Cenini et al. *Chem. Abstr.* 1972, 77, 41003m.

(List continued on next page.)

Primary Examiner—James C. Housel
Assistant Examiner—Arlen Soderquist
Attorney, Agent, or Firm—Nixon & Vanderhye

[57] ABSTRACT

Organometallic compounds such as tricarbonyl-($\eta^4$-1,3-cyclo-hexadiene)Iron(O) display an infrared spectrum which varies according to the solvent polarity, pH and similar factors. By comparing the wavenumber position and shape of the peak of a test spectrum with reference spectra by interpolation or extrapolation, information is obtained about the test sample, even a quantitative analysis in some cases. More than one organometallic compound may be used in one experiment (for double checking), and/or a mixture of analytes may be investigated, for obtaining information about the combination.

13 Claims, 10 Drawing Sheets

OTHER PUBLICATIONS

R. J. Klingler et al. *Inorg. Chem* 1981, 20, 34–40.
S. Tondu et al., *J. Chem. Soc., Chem. Commun.* 1985, 326–328.
G. Jaouen et al. *Pure & Appl. Chem.* 1985, 57, 1865–1874.
A. Vessieres et al. *Inorg. Chem.* 1988, 27, 1850–1852.
A. A. Ismail et al. *Clin. Biochem.* 1989, 22, 297–299.
I. S. Butter et al. *Appl. Spectrosc.* 1989, 43, 1497–1498.
M. Savignac et al. *J. Chem. Soc. Chem. Commun.* 1991, 615–617.
G. Patonay et al. *Appl. Spectrosc.* 1991 45, 457–461.
C. C. Barraclough et al. *J. Chem. Soc.* 1961, 2582–2584.
D. A. Brown et al. *J. Chem. Soc.* 1962, 3849–3854.
E. H. Santos et al. *J. Organomet. Chem* 1989, 375, 197–201.

SPECTROSCOPIC INVESTIGATION USING ORGANOMETALLIC COMPOUNDS

This invention relates to a method of spectroscopic investigation of analytes usually (but not necessarily) by infrared or Raman techniques, using organometallic compounds.

Infrared spectroscopy is widely employed for the direct determination of infrared-active analytes. In such work, it has long been observed that vibrating-group frequency shifts occur in infrared spectra depending on internal changes to the analyte molecule and on external changes to the environment of the vibrating group.

An advantage of using certain organometallic compounds, in particular metal carbonyls, in infrared spectroscopic analysis is that the carbonyl stretching frequencies are narrow, intense bands falling at around 2000 $cm^{-1}$, which is a part of the spectrum relatively free from interfering absorbances from the commoner solvents. This advantage is exploited according to Jaouen et al's U.S. Pat. No. 4656142, which discloses that oestrogen may be quantitatively determined by binding it to a 'designer' carbonyl-containing organometallic compound, removing surplus compound, and, from the intensity of infrared absorption, establishing the quantity of carbonyl—and hence oestrogen—present in the sample.

It is incidentally observed in the experimental plots illustrating the Jaouen patent, confirming an earlier remark above, that carbonyl frequency shifts occur between the 'designer' organometallic compound when uncombined in solution and when in the solid, bound to the oestrogen. This observation is not put to any use, indeed it does not rate a mention in the text of the patent.

We have found that the frequency shift and any change of shape of the peak can in fact convey valuable information, not as much (as might be supposed) about the vibrating group as such (carbonyl in that case) nor indeed even about only its immediate environment, but also about the environment of a functional group at a remote part of the organometallic compound. Present-day knowledge does not allow the full implications of a frequency shift or change of peak shape to be determined from first principles, and therefore we correlate an observed shift or change with reference samples.

SUMMARY OF THE INVENTION

Therefore, the present invention is a method of investigating an analyte, comprising presenting an organometallic compound to the analyte, the said compound having a probe group affected by the analyte and linked to a metal-ligand system, the said system comprising at least one infrared/Raman active group, observing the shape(s) and/or wavenumber position(s) of the peaks and/or other part(s) of the infrared/Raman spectrum of said system, comparing said shape(s) and/or position(s) with the corresponding shape(s) and/or position(s) in known analytes, and, by interpolation or extrapolation if necessary, determining a characteristic of the analyte.

The said shape(s) may be investigated by Principal Component Analysis, a statistical technique for analysing data, in this case infra-red data, to yield a small number of meaningful Principal Components, each successive Principal Component accounting for as much of the (remaining) variability of the information as possible subject to being uncorrelated with (=mathematically orthogonal to) all the previous Principal Components; each Principal Component may be described by a Score and a Weighting ("Loading"). Thus, the shape of even one peak can be made to reveal significant quantities of information.

Preferably, in the organometallic compound, the linkage between the probe group and the metal-ligand system is made by use of a common organometallic bonding mode so that the probe group is bound as a carbyne, a carbene, $\eta^n\pi$-complex (where n is preferably from 1 to 7), or a o-bound ligand. Examples of a suitable $\eta^n\pi$-complex are (where n=the number of carbon atoms $\pi$-bonded to the metal) alkene or alkyne (n=2), diene (n=4) or arene (n=6).

The probe group may be selected according to the relevant characteristic being investigated of the analyte, thus for example the probe group might be —COOH if pH is being Investigated, or an —OR substitute (R is an alkyl group) if solvent polarity is being Investigated. Other possible investigations can include a quantitative analysis of a multi-compound mixture when only the identities of the components were known.

Where the analyte is a biological receptor, to which the organometallic compound binds via the probe group, the present method can be successfully performed even in the presence of excess of the organometallic compound, because the receptor-organometallic bound combination gives rises to a spectral peak at a different wave number from the unbound (i.e. excess) organometallic compound. This is contrary to conventional wisdom, which would recommend washing away the excess organometallic compound before performing the method.

Figure 1:
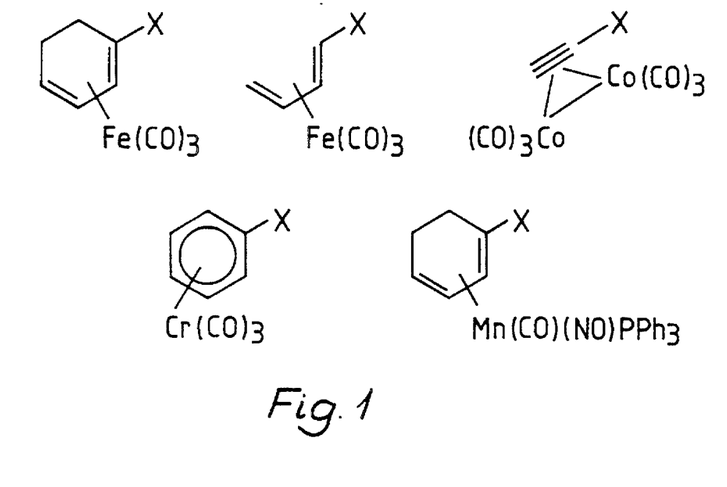
FIG. 1 shows typical examples of metal-ligand systems.

The metal-ligand system may be a carbonyl, nitrosyl, thiocarbonyl or mixture of such ("reporting groups"), and spectrally inactive (i.e. less active in Infrared/Raman) groups ("non-reporting groups") may be present, such as phosphine and arsine. Thus, examples of such systems include: $-M(CO)_x$, $-M(CO)_{x-1}PPh_3$ and $-M(NO)_{x-y}(CO)_y$ where M is a transition metal, for example, Fe, Cr, Co or Mn and x and y are integers. Typical examples of metal-ligand systems are illustrated in FIG. 1 by the structures (1)–(5): (1): M=Fe, x=3, y=0, (etc). At least one reporting group Is present, and usually more information can be gleaned If more than one reporting group is present since then more infrared bands are available for interpretation. In some applications, at least two infrared bands are necessary, and the complex must contain 2 or more carbonyl ligands (for example, in the case of the use of carbonyl reporting groups) so that sufficient vibrational modes are available.

The method of investigation, according to the invention, may extend to using two or more organometallic compounds simultaneously or sequentially on an analyte, to obtain more information e.g. about multicomponent mixtures or to secure Internal cross-confirmation of the determination. Likewise, the method may extend to investigating a mixture of analytes using one organometallic compound; in that application, the sheer amount of information tucked away In the shape of a peak, as decoded by e.g. Principal Component Analysis, can begin to be fully exploited. Similarly, the method may extend to investigating a mixture of analytes using a plurality of organometallic compounds, and in this case, either each organometallic compound may respond to a different given one of the analytes or there may be overlap in that regard.

In a typical case using one organometallic compound having a plurality of reporting groups, the infrared absorbance spectrum will show two or more sharp peaks near wavenumber 2000 $cm^{-1}$. These peaks will shift in wavenumber and shape when the probe group is presented to a different analyte. To facilitate meaningful comparison between analytes, it is advantageous in some applications, and is very much preferred according to the present invention, to normalize the different spectra obtained in different analytes, that is, apply linearly proportional corrections to the absorbance and offset corrections to wavenumber scales of all the spectra (except one) so as to make one of the peaks coincide; then all shape studies, comparisons, interpolations etc can take place using the (thus normalized) divergences of the other peak (or peaks). Two peaks represent asymmetric and symmetric vibrations respectively; either one can be used as the basis for normalization, though normalization on the basis of the symmetric peak provides a convenient general procedure since in cases where there are more than two peaks, there is one symmetric vibration but several asymmmetric, vibration modes. Both types of peaks may have to be used in case, for example, the asymmetric vibration peak for one probe-analyte system overlaps the symmetric vibration peak for another probe-analyte system in the same experiment.

The infrared/Raman spectra are typically determined by transmission measurements but different sampling techniques may be useful for special cases, for example opaque samples and aqueous samples, for which attenuated total internal reflectance spectroscopy (ATR) can be used. In the case of ATR, the signals respond in the expected way to crystal angle and refractive index, and thus the method according to the invention is amenable to the use of any of these and other sampling techniques. Crystal materials which can be used as transmission cell windows include NaCl, KBr and $CaF_2$, and, for ATR, ZnSe, ZnS and Ge, which all have their own particular combination of refractive index, wavenumber transmission range and relevant physical properties (e.g. water-solubility, cleavabillty).

BRIEF DESCRIPTION OF THE DRAWINGS

The invention will now be described in further detail with reference to the accompanying drawings in which.

EXAMPLES

The invention will now be described with reference to the following examples.

EXAMPLE 1

This example relates to measuring pH of an analyte. This is an example of the method applied to one analyte using one organometallic compound.

Tricarbonyl($\eta^4$-2,4-hexadienoic acid)iron(O), prepared by the method of Cais and Maoz (M Cais and N Moaz, J Organomet Chem 1966 5 370), was purified by chromatography on silica gel eluted with petroleum ether (40°–60° C.). The tricarbonyl iron complex (9.8 mg) was added to methanol (10 ml), the pH was slowly altered by additions of aliquots of base ($KOH_{aq}$) and the spectra were measured after each addition. The complex equilibriates according to pH as follows.

Figure 2:
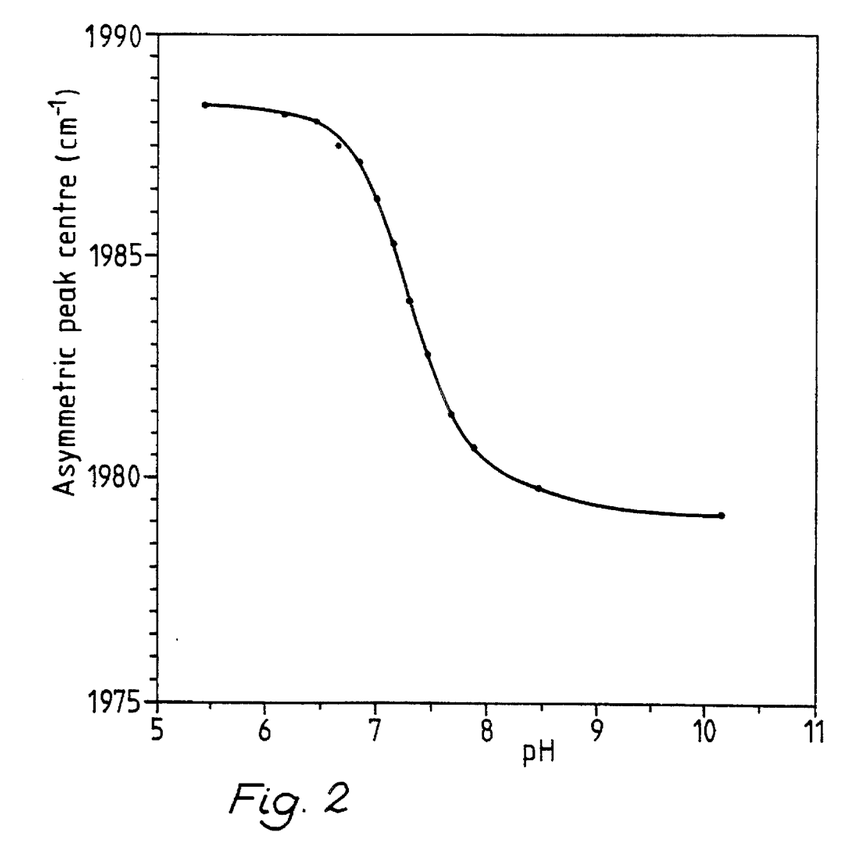
FIG. 2 shows how the position of the asymmetric peak can vary with pH.

IR spectra were recorded, averaged over 16 scans at 0.5 $cm^{-1}$ resolution using a deuterated triglycine sulphate (DTGS) detector to examine (1 ml) portions of the reaction mixture withdrawn from the reaction vessel by syringe. Each spectrum required about 6 minutes to record. A 0.5 mm path length transmission cell with $CaF_2$ windows was used to contain the sample. The sample was returned to the bulk of the reaction mixture after each spectrum was recorded. The symmetric peak was obscured due to a large absorbance peak from the methanol, so data for interpretation were taken from the asymmetric peak. The position of the asymmetric peak in the IR spectrum of the $Fe(CO)_3$ group at 13 different pH levels is shown in FIG. 2, which is a pH titration curve for the tricarbonyl($\eta^4$-2,4-hexadienoic acid)iron(O) complex. Complexes bearing carboxylic acid probe groups can be used to give an indication of pH in solution. This could be utilized in the measurement of pH of aqueous environmental samples such as rainwater, or for the examination of intracellular pH levels.

EXAMPLE 2

This example relates to quantitative analysis of a three-solvent liquid, the identities of the solvents being known. Such an analysis could be required in process control in various chemical industries. This is an example of the method applied to three analytes using one organometallic compound.

Tricarbonyl($\eta^4$-1,3-cyclohexadiene)iron(O) was prepared by the method of Birch et al, and purified by vacuum distillation. (A J Birch, P E Cross, J Lewis, D A White and S B Wild, J Chem Soc (A) 1968 p332). Three solutions were made, each containing 1 mg $ml^{-1}$ of this compound, in dimethylacetamide (D), isopropanol (P) and ethyl acetate (A). These solutions, and various mixtures thereof, were studied. In the following table, the solution 2AD is (2 ml A+1 ml D), and so on.

The infrared spectrum of the metal complex in each solvent mixture composition was recorded, 16 averaged scans, at 0.5 cm$^{-1}$ resolution using an InSb detector. Each spectrum required about 1.6 minutes to acquire. A solvent background spectrum was also recorded for each composition. Variation in both the position and shape (width In this case) of the peaks was observed. This is shown In Table 1.

TABLE 1

| Solvent Composition | Symmetric Peak (cm$^{-1}$) | Asymmetric Peak (cm$^{-1}$) | Peak Width of Symmetric (cm$^{-1}$) | Peak Width of Asymmetric (cm$^{-1}$) | Peak Height Ratio |
|---|---|---|---|---|---|
| A | 2043.5 | 1970.0 | 8.3 | 19.7 | 0.74 |
| 2AD | 2041.7 | 1967.0 | 9.7 | 22.3 | 0.72 |
| AD | 2040.8 | 1966.9 | 9.9 | 23.0 | 0.72 |
| A2D | 2040.3 | 1965.5 | 10.1 | 23.5 | 0.72 |
| D | 2039.0 | 1963.8 | 10.7 | 24.5 | 0.72 |
| 2DP | 2040.8 | 1965.8 | 10.2 | 23.5 | 0.73 |
| DP | 2041.5 | 1967.8 | 9.9 | 22.9 | 0.73 |
| D2P | 2042.6 | 1969.6 | 9.7 | 21.5 | 0.73 |
| P | 2045.5 | 1974.8 | 7.9 | 17.3 | 0.72 |
| 2PA | 2044.2 | 1972.3 | 8.5 | 19.3 | 0.73 |
| PA | 2043.9 | 1971.4 | 8.4 | 19.5 | 0.73 |
| P2A | 2043.6 | 1970.0 | 8.3 | 19.5 | 0.73 |
| ADP | 2042.1 | 1968.3 | 10.0 | 23.0 | 0.73 |

Peak height ratio is the ratio between the two absorbance maxima values.

Figure 3:
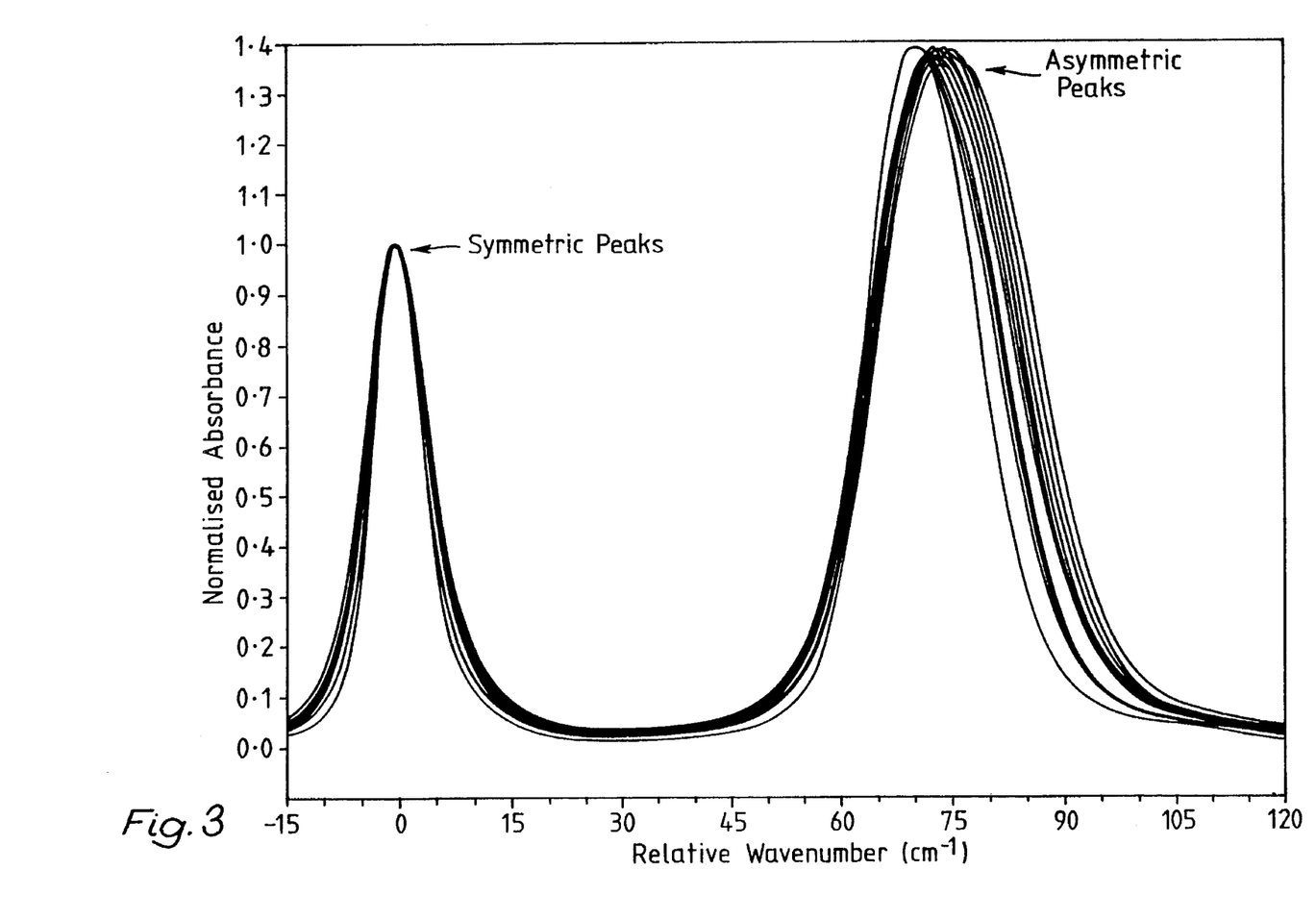
FIG. 3 is a compilation of superimposed normalized plots of solution spectra of Example 2.

The spectra were normalized ordinate-wise so that all the symmetric peak maxima coincided in height (at absorbance of 1) and were also normalized abcissa-wise so that all the peak maxima coincided laterally (at a relative wavenumber of 0). This improved the interpretation of information available from the asymmetric peak on the higher relative wavenumber side, about the point of inflection, as can be seen from the combined thus-normalized plots of the spectra, FIG. 3.

The SPSS-X statistical package was used to compute (using the command program in the appendix) the mean, standard deviation, and loadings for the measured (normalized) data points. These statistics were utilized by the computer program to generate the principal component scores (factors 1 and 2 in the case of the example in FIG. 4) for each of the solvent compositions. The information gained by principal component analysis (PCA) of the set of data obtained from a Known system can be applied to an unknown so it can be transformed into the same axes system. The transformation formula for an individual solvent composition with respect to factor 1 (where $\bar{x}_n$ and $\sigma_n$ are calculated from data obtained from all the solvent mixtures under investigation, i.e. 13 solvent compositions In the case of data shown in FIGS. 3 and 4)

$$\text{Factor 1} = \sum_{n=1}^{N} \left[ \frac{V_n - \bar{x}_n}{\sigma_n} \right] L_n$$

where:
N=Total number of variables, i.e. the number of data points in the segment of the spectrum.
$V_n$=Measured (normalized) data point for variable n.
$\bar{x}_n$=Mean of variable n for all solvent compositions.
$\sigma_n$=Standard deviation of variable n for all solvent compositions.

$L_n$=Loading for variable n for Factor 1.
(n is not the n of the $\eta^n$ complexes discussed earlier, nor is $\bar{x}$ connected with the x of earlier.)

Factor 2 is obtained in an analogous fashion using the loadings ($L_n$) generated by the SPSS-X package for the second level of significance. For the plot shown in FIG. 4, two factors are sufficient, but in principle further factors (of decreasing significance) can be used to produce multi-dimensional plots.

In this way the interpretation of data from an unknown environment can be undertaken. To perform the principal component analysis, the complete spectrum was segmented to reduce the computational power required. A complete data set for thirteen compositions from spectra measured between 4000 and 400 cm$^{-1}$ contains 187,200 data points. Even in the 2100 to 1900 cm$^{-1}$ range the number of data points Is 10,400. Segmenting also allowed the investigation of portions of the spectra to see if different parts contained similar information. Thirteen segments, each of 37 data points per composition, were examined.

Figure 4:
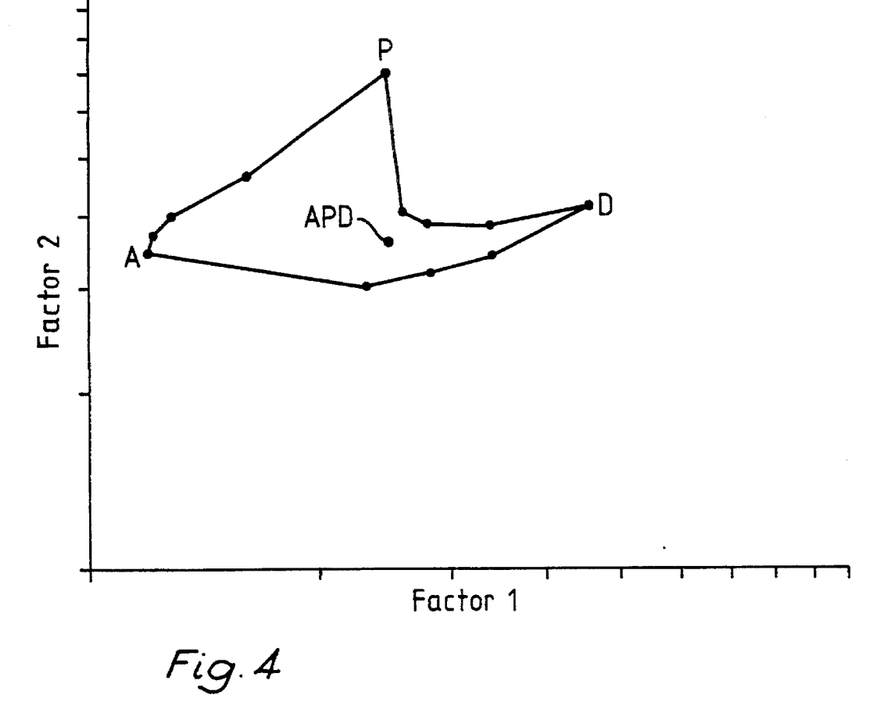
FIGS. 4 and 5 are actual and generalized PCA plots derived from the three-solvent investigation of FIG. 3.
Figure 5:
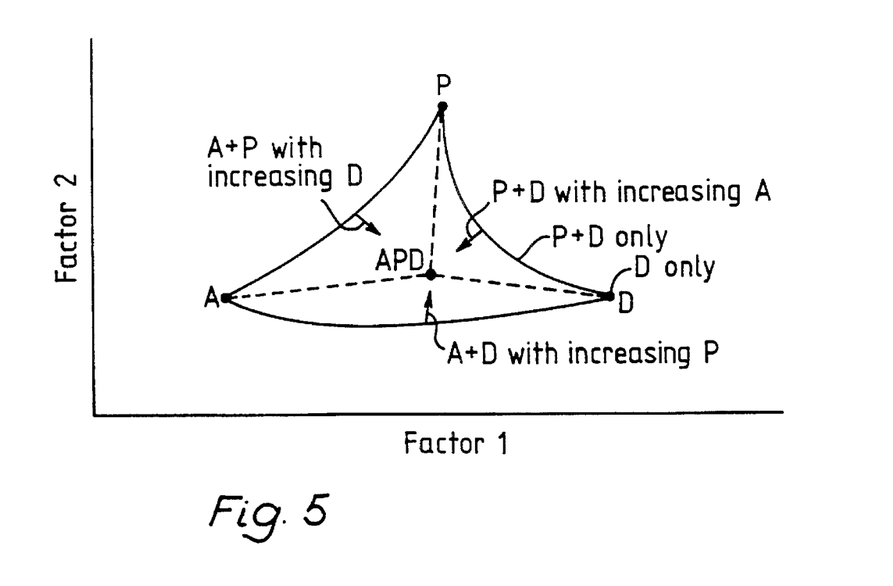

FIG. 4 shows the PCA plot from one of the segments. This portion contained the majority of the asymmetric peak on the higher relative wavenumber side. Similar results have been obtained from other segments of data, and with different numbers of data points in the segment examined. The plot of FIG. 4 is topologically equivalent to a three-component phase diagram. Thus, it consists of a "triangle" bounded by three lines each corresponding to data from a respective one of the three 2-solvent mixtures, the corners of the triangle representing measurements in each single solvent respectively. A measurement on a mixture of all three solvents appears inside the triangle. An idealized result is shown in FIG. 5. Although the diagram obtained from the experimental points is not a symmetrical triangular form, information about an unknown composition of any or all the solvents can be calculated from the spectra, using principal component analysis, by determination of where and in which region, the datum obtained from the unknown is located. This will reflect the ratio of solvents present in the unknown case.

EXAMPLE 3

This example relates to a qualitative assessment of the polarity (or other characteristic) of a solvent chosen at will.

A solution of organometallic probe reporting groups has been examined. The groups were based on the cyclic skeleton of the tricarbonyl($\eta^4$-1,3-cyclohexadiene)iron(O) complex, to which are attached various substituents at the 1,2 and 4 positions, as Indicated in table 2.

TABLE 2

| Ra | Rb | Rc | Compound Name |
|---|---|---|---|
| H | H | H | Tricarbonyl($\eta^4$-1,3-cyclohexadiene)-iron(O) |
| OCH$_3$ | H | H | Tricarbonyl($\eta^4$-1-methoxy-1,3-cyclohexadiene)iron(O) |
| H | OCH$_3$ | H | Tricarbonyl($\eta^4$-2-methoxy-1,3-cyclohexadiene)iron(O) |
| OCH$_3$ | OCH$_3$ | H | Tricarbonyl($\eta^4$-1,2-dimethoxy-1,3-cyclohexadiene)iron(O) |
| OCH$_3$ | H | OCH$_3$ | Tricarbonyl($\eta^4$-1,4-dimethoxy-1,3-cyclohexadiene)iron(O) |
| H | C$_6$H$_5$ | H | Tricarbonyl($\eta^4$-2-phenyl-1,3-cyclohexadiene)iron(O) |

Three solutions of each metal complex (1 mgml$^{-1}$) were prepared, in spectroscopic grade hexane, tetrahydrofuran (THF) and dimethyl acetamide respectively. A spectrum of each solution was recorded, 16 averaged scans per spectrum, at 0.5 cm$^{-1}$ using the InSb detector. Each spectrum required about 1.6 minutes to record. A solvent background spectrum was also recorded for each.

IR spectra were measured in fifteen different solvents, viz. (1) Hexane; (2) Cyclohexane; (3) Toluene; (4) Dichloromethane; (5) Diethylether; (6) Tetrahydofuran (THF); (7) Acetonitrile; (8) Ethyl acetate; (9) Acetone (propan-2-one); (10) Methanol; (11) 1-Octanol; (12) Dimethyl formamide (DMF); (13) Dimethyl acetamide (DMAc); (14) Acetic anhydride; and (15) water. For nonpolar solvents both the symmetric and asymmetric bands were found to be at relatively higher wavenumbers. Also for nonpolar solvents the bands were sharper, and for the cases of n-hexane and cyclohexane, the asymmetric peak was resolved into two bands which overlapped.

Figure 6:
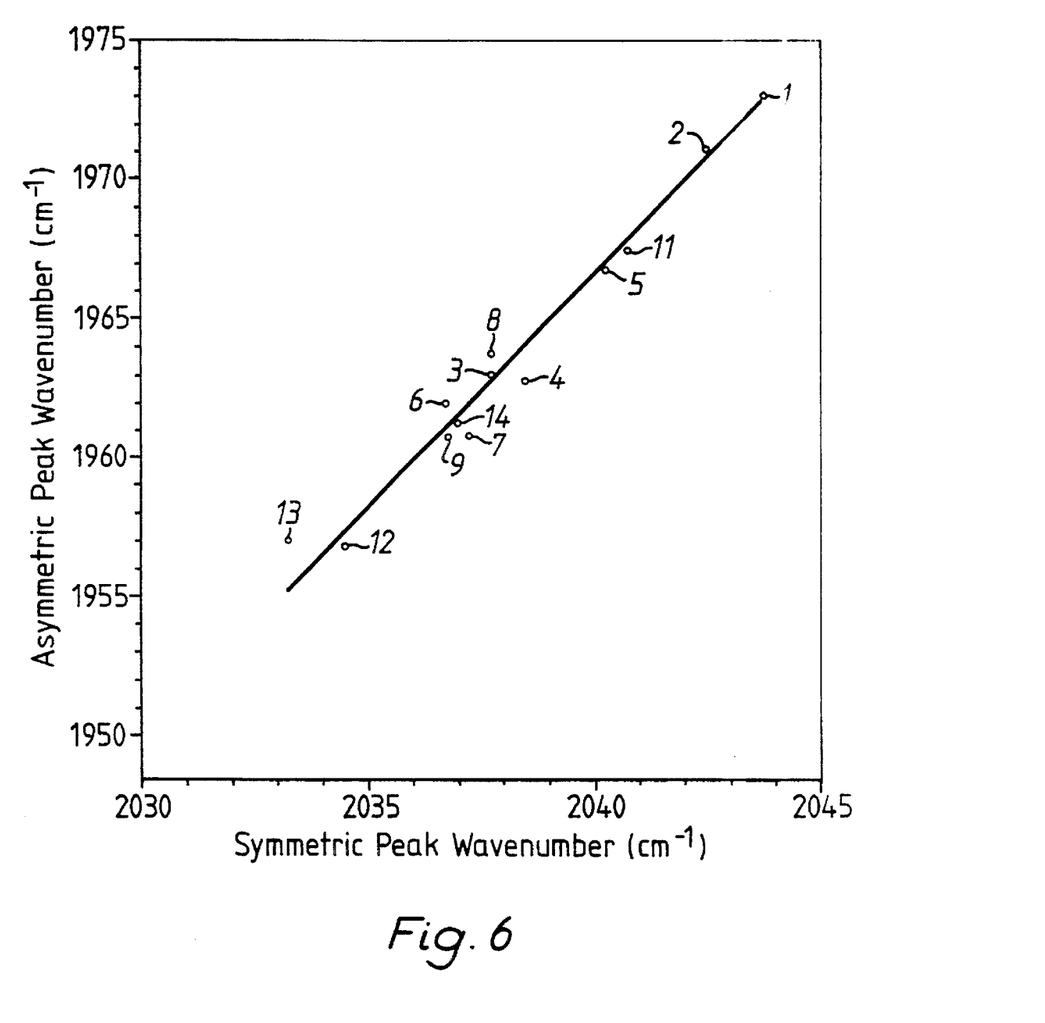
FIG. 6 is a correlation between peak wavenumbers by solvent.

FIG. 6 shows the correlation obtained in the case of the 1-methoxy substituted cyclohexadiene complex between the peak wavenumber position for the symmetric and asymmetric bands measured from thirteen spectra each recorded In a single solvent identified by the number shown in the figure. Other substituents and substitution patterns, examined in a representative selection of solvents, gave similar results. The other solutes listed Tables 2 and 3 showed the same trends in the effect of solvent polarity, but for a single solvent the infrared band position need not necessarily be similar and may be displaced to either higher or lower wavenumbers. All the solutes in all of the different solvents gave plots of similar slopes but the range, i.e. the linear distance from the highest wavenumber compound (taken as n-hexane) to the lowest, (DMAc), is not constant. The ranges measured for different substitution types and patterns of solute are shown in table 3.

The Information gained about the range is important for the optimization of environment-sensitivity measurement. (The change in the range In Table 3 is about seven wavenumbers). The larger the range, the greater the sensitivity of the probe to its environment. Taking the unsubstituted diene as the reference point, Introducing a substituent into the 2 position appears to suppress the range. Conversely substituents in the 1 position extend the range. When there are two substituents on the ring there can be conflicting influences. For the case of the tricarbonyl($\eta^4$-1,2-dimethoxy-1,3-cyclohexadiene)iron(O) the effect of the 1-methoxy group is overcome by the suppression of the range by the 2-methoxy substituent.

Since positions 3 and 4 are equivalent to positions 2 and 1 respectively, due to a mirror plane, tricarbonyl($\eta^4$-1,4-dimethoxy-1,3-cyclo-hexadiene)iron(O) can be considered to have two methoxy groups in the 1 position, (i.e. two terminal substituents on the diene). This gives the largest range In the set of compounds measured.

In measurement of unknown solvents, infrared data can be interpreted by reference to plots of the type illustrated in FIG. 6 to give an indication of the hydrophobicity or hydrophilicity of the unknown. The best resolution of environments requires the use of substitution patterns with the largest range values indicated In table 3.

TABLE 3

| Compound | Range (cm$^{-1}$) | Relative range (cm$^{-1}$) |
|---|---|---|
| Tricarbonyl($\eta^4$-1,4-dimethoxy-1,3-cyclohexadiene)iron(O) | 21.3 | +3.3 |
| Tricarbonyl($\eta^4$-1-methoxy-1,3-cyclohexadiene)iron(O) | 19.7 | +1.7 |
| Tricarbonyl($\eta^4$-1,3-cyclohexadiene)iron(O) | 18.0 | 0 |
| Tricarbonyl($\eta^4$-2-methoxy-1,3-cyclohexadiene)iron(O) | 17.4 | −0.6 |
| Tricarbonyl($\eta^4$-1,2-dimethoxy-1,3-cyclohexadiene)iron(O) | 16.9 | −1.1 |
| Tricarbonyl($\eta^4$-2-phenyl-1,3-cyclohexadiene)iron(O) | 14.3 | −3.7 |

Environment sensitivity effects are not restricted to the tricarbonyliron probe group (Fe(CO)$_3$) attached to a diene compound. Two other metal/ligand systems, chosen because of their proven utility in bio-assay methods, have been examined to illustrate the generality of the environment-sensitive reporting group phenomenon. These showed similar correlations between solvent polarity and infrared spectral characteristics, and had different range characteristics for the resolution of environment differences. The complexes used are (a) tricarbonyl-($\eta^6$-chlorobenzene)chromium(O) and (b) hexacarbonyl(2-propyn-1-ol)dicobalt(O).

Figure 7A:
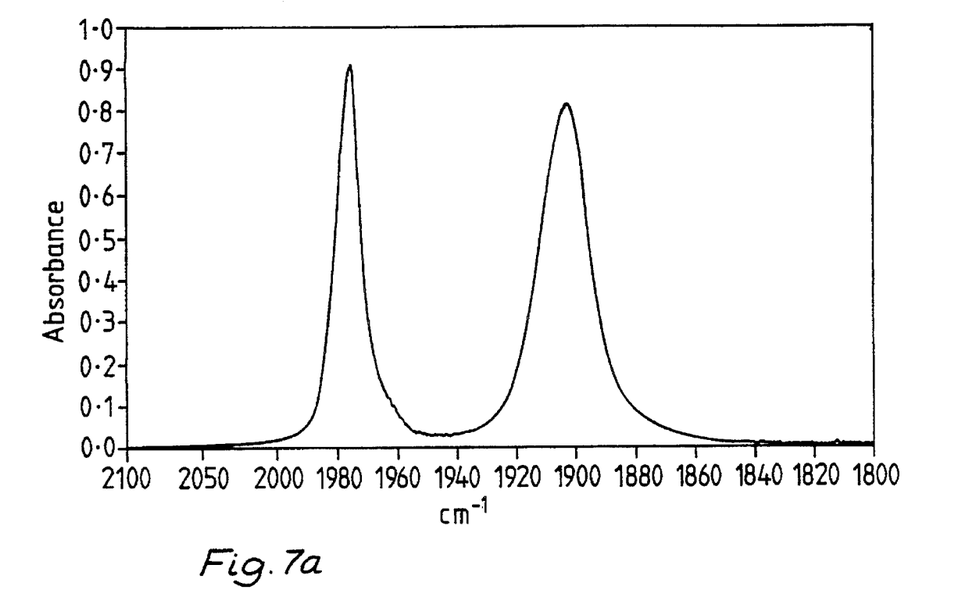
FIGS. 7a and 7b show absorption spectra for two complexes.
Figure 7B:
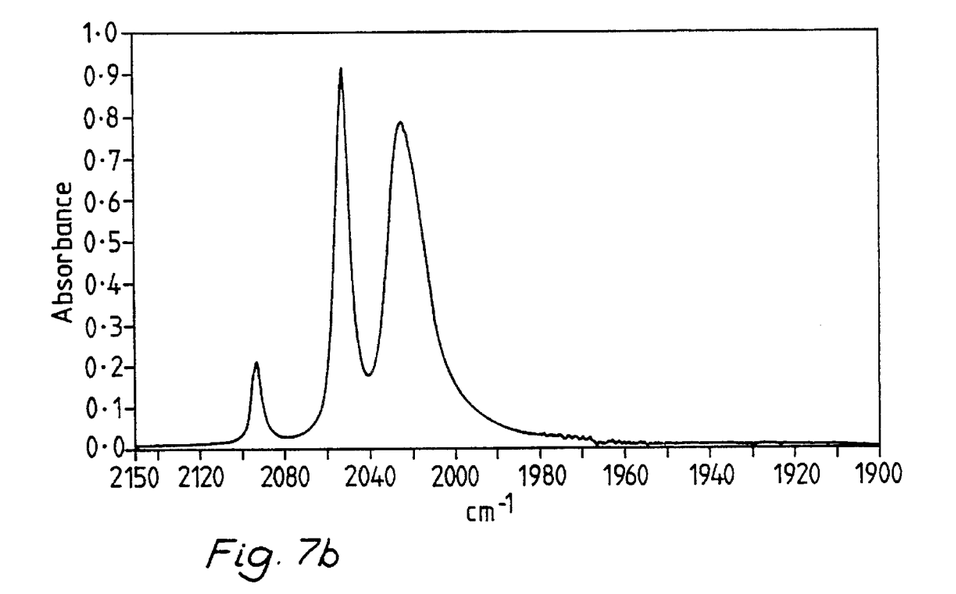

FIG. 7 shows the background-corrected spectra for both these complexes in tetrahydrofuran THF. In spectrum (b) there is an extra band, at about 2095 cm$^{-1}$.

Figure 8A:
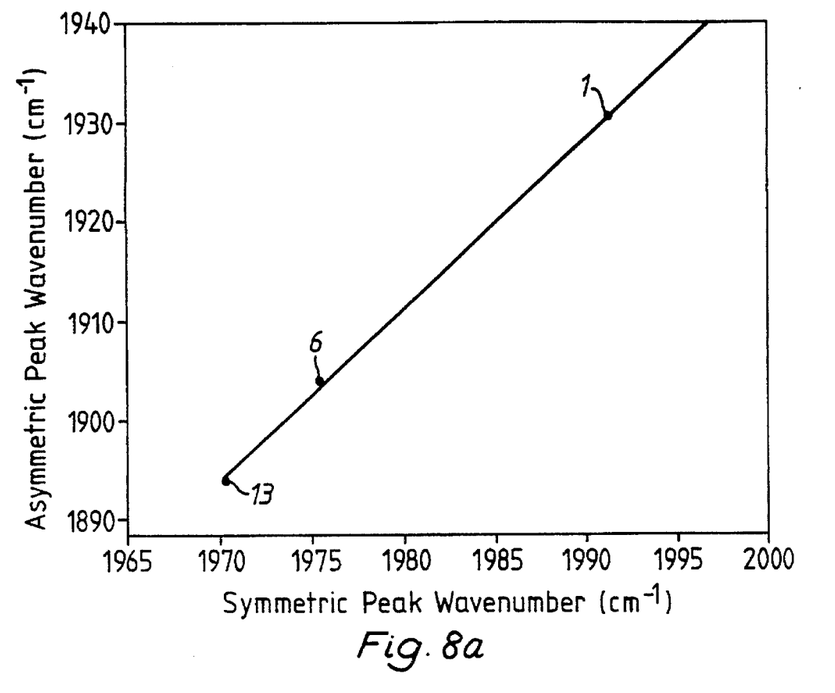
FIGS. 8a and 8b are correlations corresponding to FIG. 6 but for other solutes.
Figure 8B:
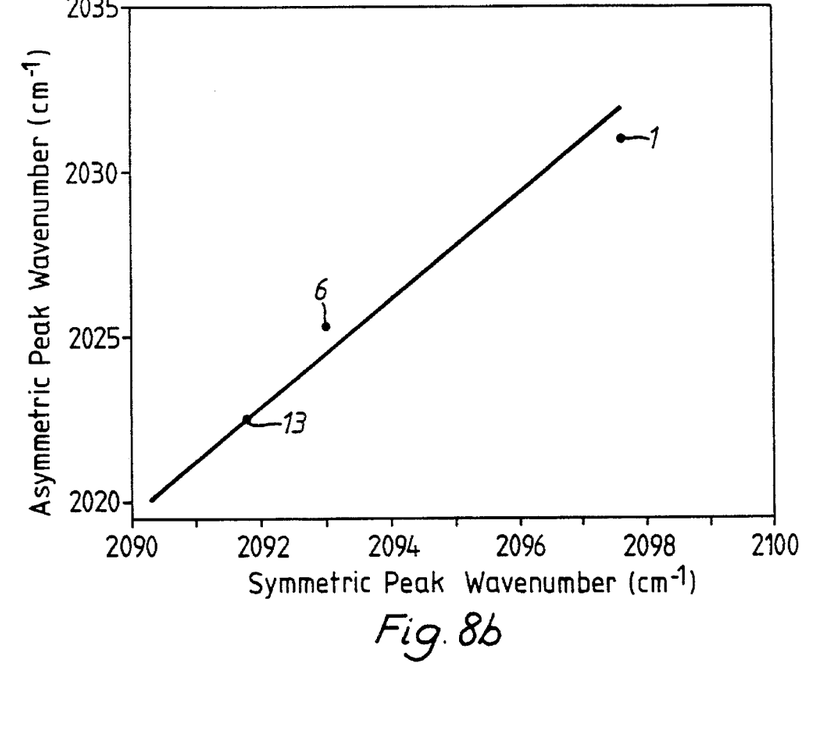

By the construction of plots of one stretching frequency against another, for each of the compounds, similar trends have been identified. This is Illustrated In FIG. 8. In hydrophobic solvents, the bands are displaced to higher wavenumbers, (see tables 4 and 5) than in correspondingly hydrophillic environments. Comparing the three metal systems It Is clear that the environment dependent wavenumber shift Is not restricted to a particular choice of metal. The metal serves only to locate the signals in a particular range of frequencies of the spectrum. Tricarbonyl iron complexes have infrared bands that are centered about 2000 cm$^{-1}$, whereas the organochromium and organocobalt absorbances are located around 1940 and 2050 cm$^{-1}$, respectively.

TABLE 4

Tricarbonyl($\eta^6$-chlorobenzene)chromium(O) in hexane, tetrahydofuran (THF) and dimethylacemide (DMAc).

| Solvent Number (see table 3 FIG. 7) | Solvent | Symmetric peak (cm$^{-1}$) | Asymmetric peak (cm$^{-1}$) | Width of Symmetric (cm$^{-1}$) | Width of Asymmetric (cm$^{-1}$) |
|---|---|---|---|---|---|
| 1 | Hexane | 1991.3 | 1930.5 | 2.2 | 9.7 |
| 6 | THF | 1975.3 | 1903.8 | 9.3 | 19.8 |
| 13 | DMAc | 1970.3 | 1893.8 | 12.1 | 25.7 |

TABLE 5

Hexacarbonyl($\eta^2,\eta^2$-2-propyn-1-ol)dicobalt(O) complex in hexane, tetrahydofuran (THF) and dimethylacemide (DMAc).

| Solvent Number (see table 3 FIG. 7) | Solvent | Band 1 ($cm^{-1}$) | Band 2 ($cm^{-1}$) | Band 3 ($cm^{-1}$) | Width 1 ($cm^{-1}$) | Width 2 ($cm^{-1}$) | Width 3 ($cm^{-1}$) |
|---|---|---|---|---|---|---|---|
| 1 | Hexane | 2097.6 | 2058.3 | 2031.0 | 2.9 | 3.5 | 13.8 |
| 6 | THF | 2093.0 | 2052.5 | 2025.3 | 5.7 | 8.3 | 20.2 |
| 13 | DMAc | 2091.8 | 2051.3 | 2022.5 | 7.7 | 10.6 | 23.9 |

Environment information can thus be obtained from two separate regions of the M-CO adsorption region of the infrared spectrum, if two complementary metal carbonyl complexes are employed in the same experiment. Thus measurements using dual probes (containing two different organometallic groups) can be undertaken.

In some cases changes in the metal-ligand system (e.g. replacement of CO by a phosphine or phosphite, replacement of the metal by an Isoelectronic metal, or more extensive changes involving non-isoelectronic metal used with alternative ligands such as cyclopentadienyl or NO) can result in substantial shifts in the position of the main environment-sensitive IR band. This is illustrated by the data presented in table 6 which demonstrates that both CO and NO bands respond to changes in solvent.

TABLE 6

Carbonyl($\eta^4$-5,6-dimethylcyclohexa-1,3-diene)(nitrosyl)(triphenyl phosphine)manganese(O) complex in hexane, tetrahydrofuran (THF) and dimethylacetamide (DMAc).

| Solvent Number (see Table 3) FIG. 7) | Solvent | Position of CO Band ($cm^{-1}$) | Position of NO Band ($cm^{-1}$) | Width of CO Band ($cm^{-1}$) | Width of NO Band ($cm^{-1}$) |
|---|---|---|---|---|---|
| 1 | Hexane | 1955.0 | 1703.5 | 12.4 | 12.5 |
| 6 | THF | 1942.3 | 1695.8 | 17.9 | 17.7 |
| 13 | DMAc | 1936.0 | * | 23.9 | * |

*Peak not resolved

Using complementary metal-containing probe groups, information can be obtained about two different aspects of the environment of the probe, e.g. pH, hydrophobicity, a binding site, etc., simultaneously. Alternatively, two independent simultaneous determinations of the same parameter can be undertaken, thus improving analytical accuracy/precision. This ability to obtain, simultaneously, differing type of data is an advantage over other techniques such as radio-isotope labelling.

EXAMPLE 4

This example relates to the use of organometallic probe groups to perform measurements in aqueous solutions. This is important when environment-sensitive probes are to be employed for the study of biological systems.

The water-soluble complex was prepared by the method of Kane-Maguire et al. and purified by precipitation from acetonitrile/ether. (T I Odiaka and L A P Kane-Maguire, J Chem Soc, Dalton Trans 1981 p1162). This compound is sparingly soluble in water but solubility is improved by a factor of two by exchanging the $PF_6^-$ counterion for chloride ion from tetra-n-butylammonium chloride.

Figure 9:
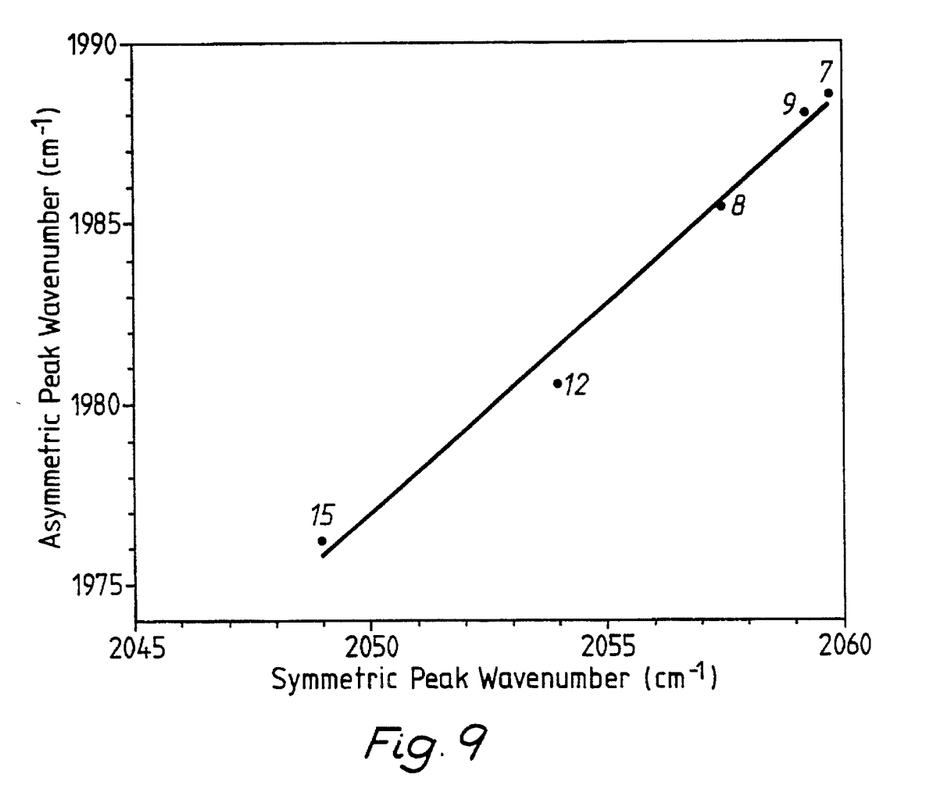
FIG. 9 is another correlation demonstrating that water can be used as a solvent with suitable solutes.

Examination of the infrared properties of this complex in different solvents indicates that environment-sensitivity properties are retained. This is indicated in the plot of symmetric and asymmetric peak positions measured in acetonitrile, ethyl acetate, acetone, DMF, and water, shown in FIG. 9. Data obtained from the water soluble probe group are consistent with data obtained from .simple .probe groups numbered as given in Example 3 above.

EXAMPLE 5

This example describes the synthesis of an analogue of the trlcarbonyliron complex of sorbic acid, and demonstrates Its use as an organometallic compound in a method according to the invention for measuring pH of an analyte. The V(CO) stretching vibrations for (In particular) the dicarbonyl-triphenylphosphineiron complex of sorbic acid are at different wavenumber values from the V(CO) stretching vibrations of the tricarbonyl compound. The two complexes also have pKa values which are different. The difference In pKa values extends the range over which the pH of a solution can be accurately measured. Together, the two organometallic compounds act as a dual sensor, independently (i.e. double-checkingly) measuring the pH of the sample solution, in a single experiment.

Synthesis of a dlcarbonyltriphenylphosphineiron complex of sorbic acid.

20 mg (0.039 mmol) of ethyl dicarbonyl($\eta^4$-2,4-hexadienoate)triphenylphosphineiron(O) was dissolved in the minimum amount of tetrahydrofuran. 50 ml of 0.1M potassium hydroxide was added, under nitrogen gas, and was then heated to 68° C. The reaction was monitored by thin layer chromatography until no starting material remained, approx. 2 hours. The reaction mixture was then acidified and extracted with ether to give yellow crystals (yield 43%). $H^1$-NMR (90 MHz, $CDCl_3$) $C_6H_5$ 7.4 ppm HC=CH 5.7, 4.9 ppm and $CH_3$ 3.2 ppm.

Preliminary studies of the tricarbonyliron and dicarbonyltriphenylphosphineiron complexes of sorbic acid.

Figure 10:
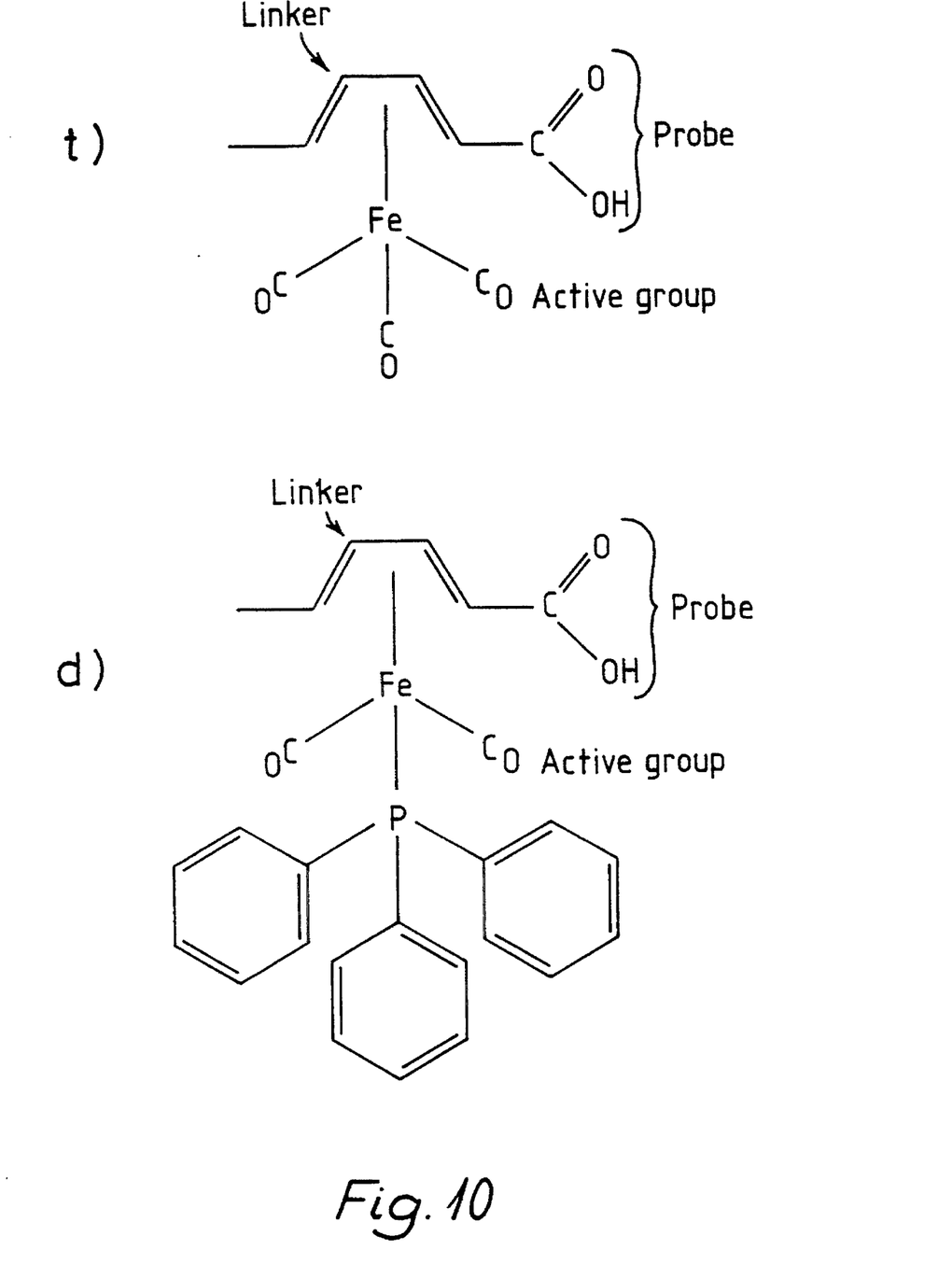
FIG. 10 shows the structure of two organometallic compounds which can be used in the method according to invention (10t being tricarbonyl ($\eta^4$-2,4-hexadienoic acid) iron (0), otherwise called the tricarbonyliron complex of sorbic acid, and 10d being dicarbonyl ($\eta^4$-2,4-hexadienoic acid) triphenylphosphineiron (0)

The structures of the tricarbonyliron and dicarbonyltriphenylphosphineiron complexes of sorbic acid (2,4-hexadienoic acid) are shown in FIG. 10, as t and d respectively. The two positions of the symmetric and asymmetric carbonyl stretching vibrations of tricarbonyliron and dicarbonyltriphenylphosphineiron groups are given in the following table. The measurements were made in a 60/40 water-methanol solution (pH 2.9) using a transmission cell with calcium fluoride windows and a 0.05 mm spacer.

| | Symmetric Band $V_s$ ($cm^{-1}$) | Asymmetric Band $V_{as}$ ($cm^{-1}$) | Separation ($cm^{-1}$) |
|---|---|---|---|
| tricarbonyl-(2,4-hexadienoic acid)iron | 2059.0 (ts) | 1990.6 (ta) | 68.4 |
| dicarbonyl(2,4-hexadienoic acid)triphenylphosphineiron | 1985.6 (ds) | 1927.5 (da) | 61.5 |

The asymmetric stretching vibration of the tricarbonyliron complex of sorbic acid ("ta", in the table) absorbs in the same range as that of the symmetric band of "ds", the dicarbonyltriphenylphosphineiron complex of sorbic acid; therefore these carbonyl stretching modes cannot be utilized for independent measurement of pH. The other stretching frequencies, "ts" (symmetric for the tricarbonyliron) and "da" (asymmetric for the dicarbonyltriphenylphosphineiron) are separated by 131.5 $cm^{-1}$ and so can be utilized for the dual independent measurement of pH.

The pH titration of the dicarbonyltriphenyl-phosphineiron complex of sorbic acid. (cf.ds. da).

Figure 11:
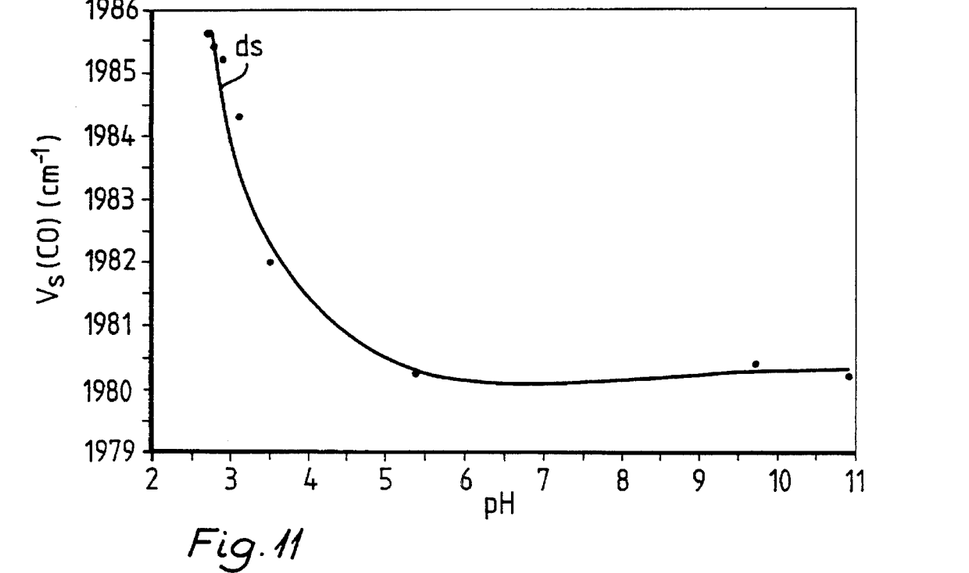
FIG. 11 is a plot of the wavenumber position of the "symmetric" carbonyl absorption peak of the FIG. 10d compound against pH.
Figure 12:
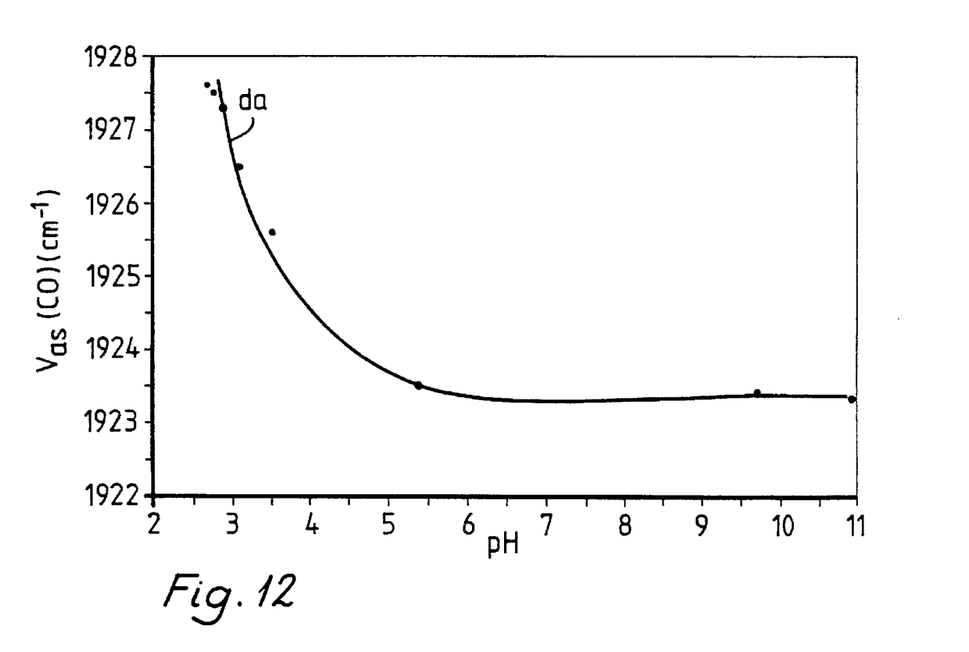
FIG. 12 is an otherwise identical plot of the "asymmetric" peak.

4 mg (0.01 mmol) dicarbonyl(2,4-hexadienoic acid)triphenylphosphineiron was dissolved in 4 ml of pure methanol. To this was added 6 ml of pure water. The solution was adjusted to approximately pH 3.0. Aliquots of 0.1 M potassium hydroxide were added, and a spectrum was recorded after each addition. The conditions used to record the spectra were a transmission liquid cell (0.05 mm spacer), 16 scans per spectrum with a resolution of 0.5 $cm^{-1}$. The position of the center of the symmetric and asymmetric carbonyl stretches are calculated at half peak height and are plotted against the measured pH, FIGS. 11 and 12. The positions of both $V_s(CO)$ and $V_{as}(CO)$ stretching vibrations change with respect of pH, giving curves "ds" and "da" respectively. It can be seen that the shape of the curves for both the symmetric and asymmetric carbonyl vibrations are similar, as expected, indicating that they both are influenced by the dissociation of the dicarbonyltriphenylphosphineiron complex of sorbic acid. Since both of the organometallic carbonyl stretching modes are affected by the change in pH, either may be used to monitor pH. This result is similar to that obtained with the sorbic acid tricarbonyliron complex, although the pKa values are different.

The pH titration of the tricarbonyliron and the dicarbonyltriphenylphosphineiron complexes of sorbic acid (cf.ts. da).

Figure 13:
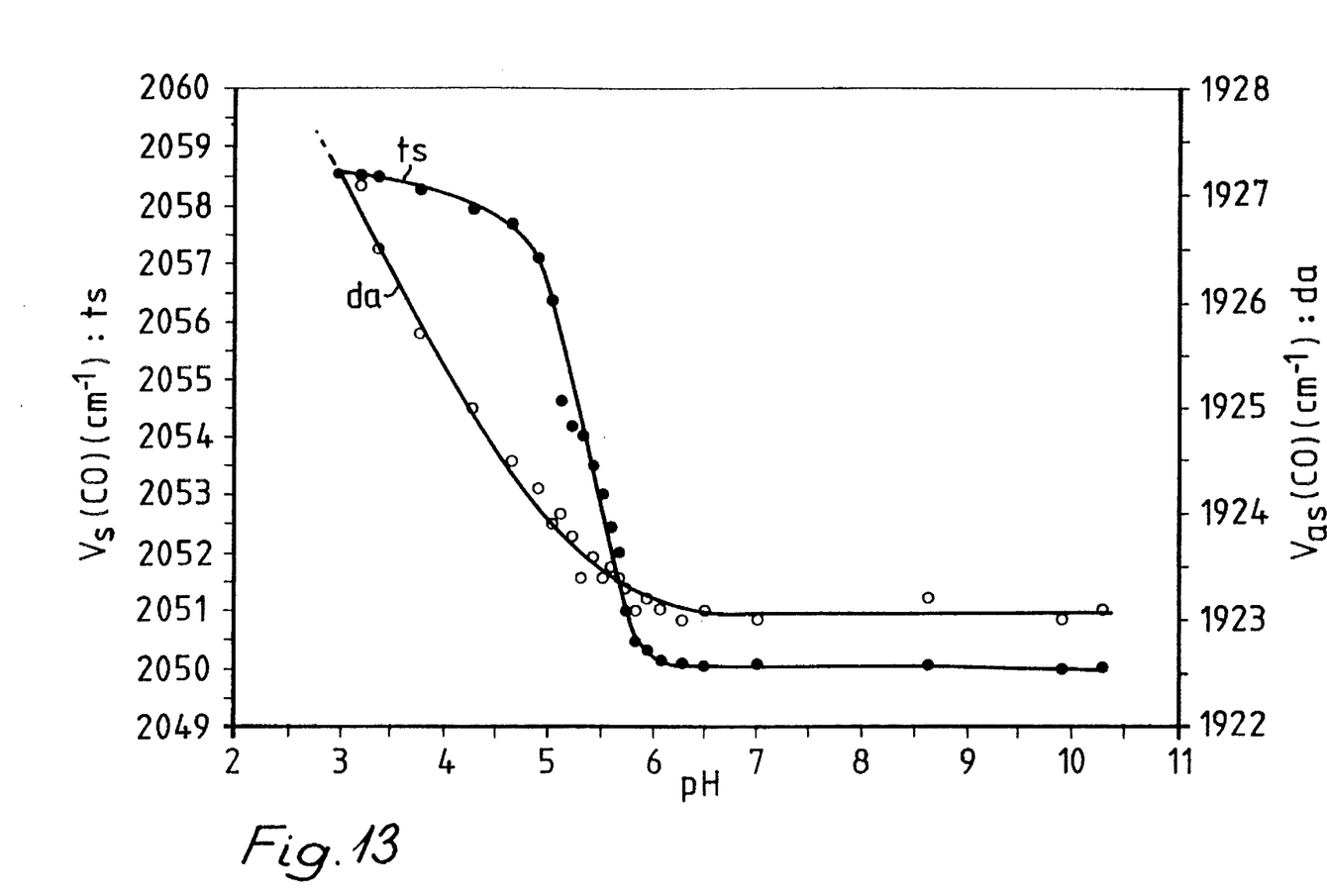
FIG. 13 is a superimposition on the same Figure (but note different axes) of FIG. 12 and of a plot of the wavenumber position of the "symmetric" carbonyl absorption peak of the FIG. 10t compound against pH using data obtained from single spectra (at each pH value) of a mixture of the two compounds in solution.

10 mg (0.04 mmol) the tricarbonyliron complex of sorbic acid and 5 mg (0.01 mmol) of the dicarbonyltriphenylphosphineiron complex of sorbic acid were dissolved in 4ml of pure methanol, to this was added 6ml of pure water. The solution was adjusted to approximately pH 3.0. Aliquots of 0.1 M potassium hydroxide were added, and a spectrum was recorded after each addition. The conditions used to record the spectra were a transmission liquid cell (0.05 mm spacer) 16 scans per spectrum, with a resolution of 0.5 $cm^{-1}$. The position of the center of the carbonyl frequencies for the $V_s(CO)$ stretching mode of the tricarbonyliron and the $V_{as}(CO)$ mode of the dicarbonyltriphenylphosphineiron (calculated at half peak height) were plotted in FIG. 13 (note: on different axes for convenience) against the measured pH. The stretching frequencies for both the vibrations change with pH (being equivalent to "ts" and "da" respectively at pH 2.9), providing independent measurement of pH in the sample. This demonstrates the principle of simultaneous dual sensing.

Appendix

10 Title "Normalized data 2 dimention SLICE 78 TO 87 RCM-1"
20 set length=none
30 file handle F1/name='SLICE.DAT'
40 data list file=F1 records=1
50 /1ID 1–4 (a)
AR1 9–15 (3) AR2 17–23(3) . . . AR37 XXX—XXX (3)
70 file handle s1/name='s1.sav'
80 save outfile=s1
90 factor variables=AR1 to AR37
100 /criteria=factors(3)
110 /rotate=varimax
120 /format=sort
130 /PRINT=UNIVARIATE INITIAL CORRELATION SIG EXTRATION
140 ROTATION FSCORE
150 plot=eigen rotation(1,2)
160 save reg(3,fact)
170 list cases cases=from 1 to 13
180 variables=id, fact1 to fact3
190 plot plot=fact2 with fact1
200 finish Line 10 only details the title of the program, so different runs can easily be identified. To save paper, line 20 prevents each section being printed on a separate page.

We claim:

1. A method of investigating the pH of a solution, said method comprising the steps off
   mixing an organometallic compound with the solution, said organometallic compound having a —=COOH probe group affected by the pH of the solution and linked to a metal-ligand system, said system comprising at least one group active in the infrared or Raman region of the spectrum;
   observing the shape(s) of spectral response curves and/or wavenumber position(s) of peaks of spectral response curves of that region of the spectrum of said system;
   comparing said shape(s) and/or position(s) with the corresponding shape(s) and/or position(s) in known solutions; and
   determining the pH of the solution by interpolation or extrapolation if necessary.

2. A method according to claim 1, wherein in the organometallic compound, the linkage between the —COOH probe group and the metal-ligand system is formed by use of a common organometallic bonding mode so that the probe group is bound as a carbyne, a carbene, an $\eta^n\pi$-complex or a $\sigma$-bound ligand.

3. A method according to claim 2, wherein n is from 1 to 7.

4. A method according to claim 1, wherein the metal-ligand system is a carbonyl, nitrosyl, thiocarbonyl or mixture of such.

5. A method according to claim 4, wherein a group less active than the carbonyl, nitrosyl, thiocarbonyl or mixture in infrared/Raman is also present.

6. A method according to claim 5, wherein said less active group is phosphine or arsine.

7. A method according to claim 4, wherein the metal-ligand system is —$M(CO)_x$, —$M(CO)_{x-1}PPh_3$ or —$M(NO)_{x-y}(CO)_y$ where M is a transition metal, and x and y are integers.

8. A method according to claim 1, wherein two or more organometallic compounds are used simultaneously or sequentially on a solution, to obtain more information.

9. A method according to claim 1, wherein, to facilitate meaningful comparison between solutions, the different spectra obtained in different solutions are normalized by applying linearly proportional corrections to the absorbance and offset corrections to wavenumber scales of all the spectra except one so as to make one of the peaks coincide whereby said interpolation or extrapolation takes place using the thus normalized divergences of the other peak or peaks.

10. A method according to claim 1, wherein the shape of the spectrum is investigated by Principal Component Analysis.

11. A method according to claim 1, wherein the shape of a peak in the spectrum is observed.

12. A method according to claim 1, performed in the presence of excess of the organometallic compound.

13. A method according to claim 1 comprising using two or more organometallic compounds and/or investigating a mixture of solutions.

* * * * *